United States Patent
Jordfald et al.

(10) Patent No.: US 6,547,739 B2
(45) Date of Patent: Apr. 15, 2003

(54) TRANSESOPHAGEAL PROBE WITH IMPROVED CONTROL PANEL

(75) Inventors: Dag Jordfald, Horten (NO); Jon Ronander, Tonsberg (NO); Jonathan Edvard Snyder, Park City, UT (US); Jiayu Chen, Palo Alto, CA (US); Joseph E. Piel, Jr., Scotia, NY (US); Karl Jonsberg, Tonsberg (NO)

(73) Assignee: GE Medical Systems Global Technology Company LLC, Waukesha, WI (US)

(*) Notice: Subject to any disclaimer, the term of this patent is extended or adjusted under 35 U.S.C. 154(b) by 84 days.

(21) Appl. No.: 09/756,305

(22) Filed: Jan. 8, 2001

(65) Prior Publication Data
US 2002/0095088 A1 Jul. 18, 2002

(51) Int. Cl.⁷ .................... A61B 8/12; A61B 1/005; H01H 13/06
(52) U.S. Cl. .............. 600/462; 600/121; 600/131; 600/133; 600/198
(58) Field of Search .................. 600/103, 122, 600/131, 133, 146, 152, 198, 462, 463, 121; 604/528

(56) References Cited

U.S. PATENT DOCUMENTS

| | | | | |
|---|---|---|---|---|
| 4,543,960 A | * | 10/1985 | Harui et al. | 600/462 |
| 5,197,178 A | | 3/1993 | Lichte et al. | 29/428 |
| 5,390,661 A | * | 2/1995 | Griffith et al. | 600/114 |
| 5,398,689 A | * | 3/1995 | Connor et al. | 600/459 |
| 5,469,852 A | | 11/1995 | Nakamura et al. | 128/662.06 |
| 5,479,930 A | * | 1/1996 | Gruner et al. | 600/146 |
| 5,489,256 A | * | 2/1996 | Adair | 600/123 |
| 5,490,522 A | * | 2/1996 | Dardel | 600/461 |
| 5,634,466 A | * | 6/1997 | Gruner | 600/136 |
| 5,685,311 A | * | 11/1997 | Hara | 600/393 |
| 5,748,114 A | | 5/1998 | Koehn | 341/22 |
| 5,872,527 A | | 2/1999 | Yanagisawa | 341/22 |
| 5,873,814 A | * | 2/1999 | Adair | 348/65 |
| 5,910,105 A | * | 6/1999 | Swain et al. | 600/104 |
| 6,142,941 A | * | 11/2000 | Benhalima et al. | 600/439 |

FOREIGN PATENT DOCUMENTS

| | | |
|---|---|---|
| DE | 198 44 614 C1 | 11/2000 |
| EP | 1 017 076 A2 | 7/2000 |
| WO | WO 98/11577 | 3/1998 |

OTHER PUBLICATIONS

International Search Report—International Application No. PCT/US 02/00611 dated Aug. 20, 2002.

* cited by examiner

*Primary Examiner*—Michael Powell Buiz
*Assistant Examiner*—Ramesh Krishnamurthy
(74) *Attorney, Agent, or Firm*—McAndrews, Held & Malloy, Ltd.; Peter J. Vogel; Michael A. Dellapenna

(57) ABSTRACT

A multiplane transesophageal probe (20) includes a transducer (28) and a handle (30). The handle incorporates a control (40) mounting switches (51–58). The switches and control panel are covered with foil (43). A seal (70) couples the control panel and foil to the handle.

14 Claims, 2 Drawing Sheets

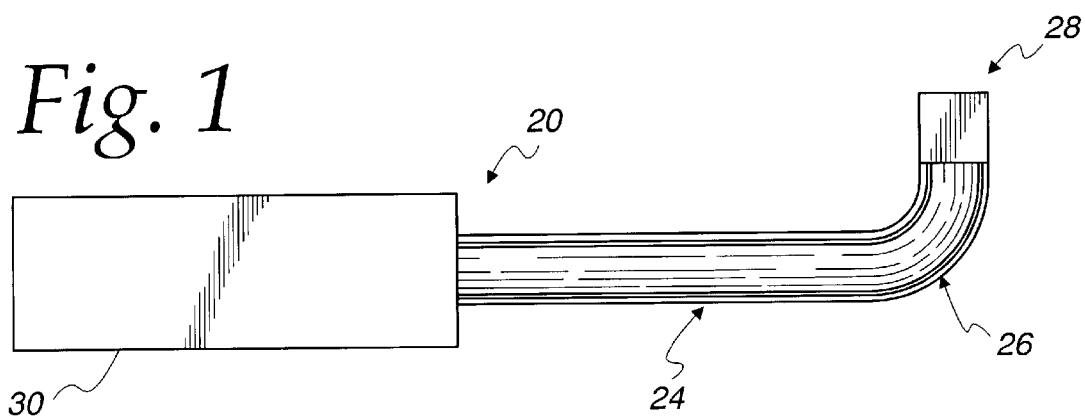
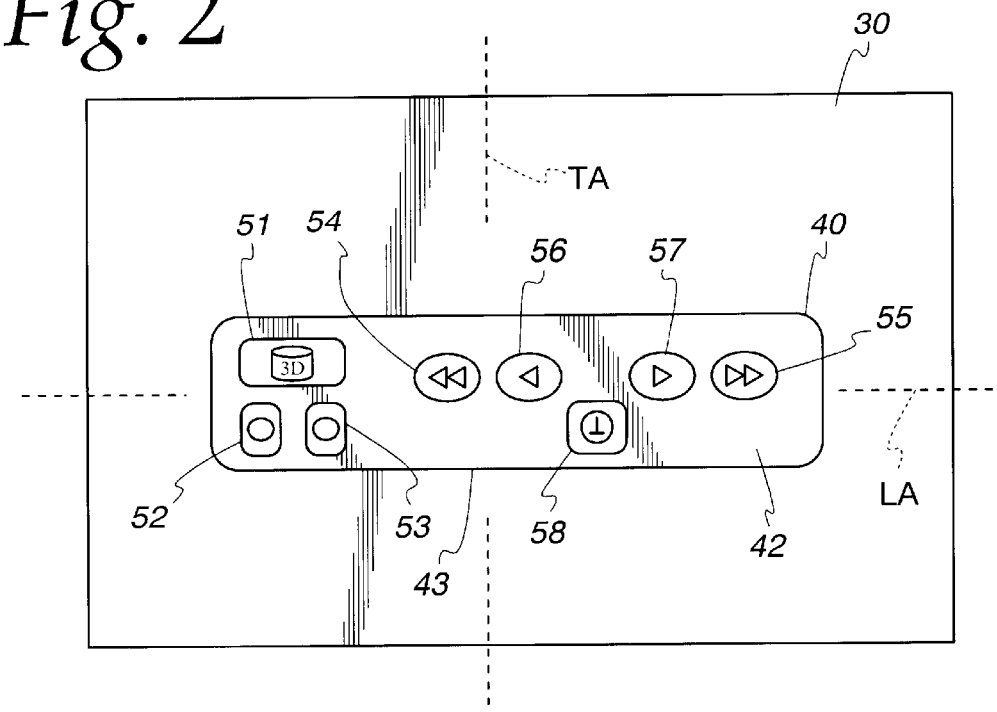
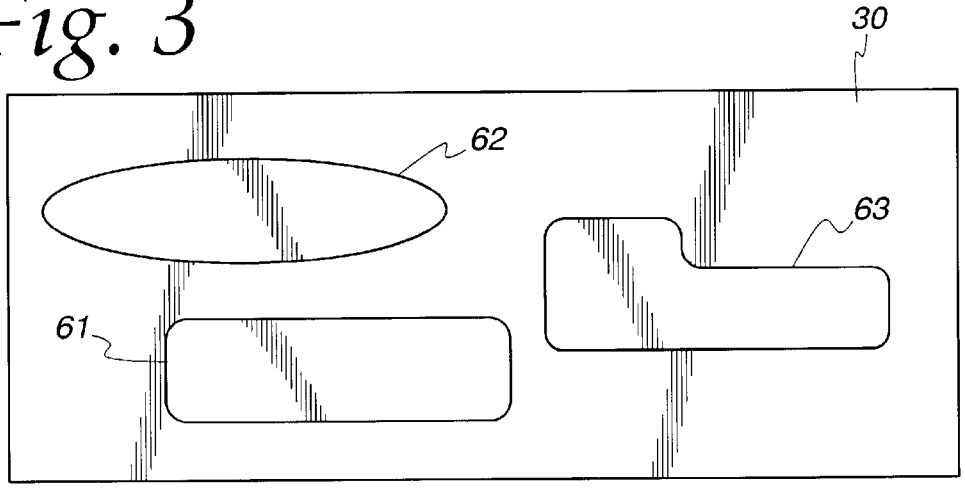

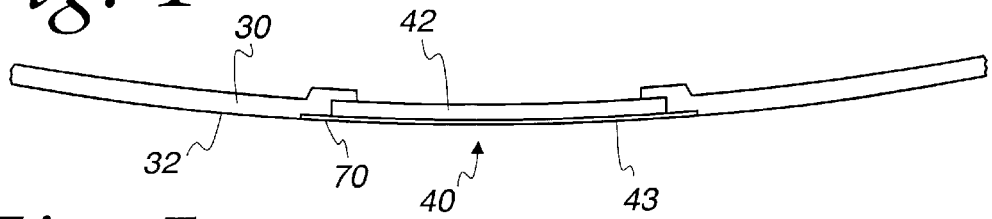
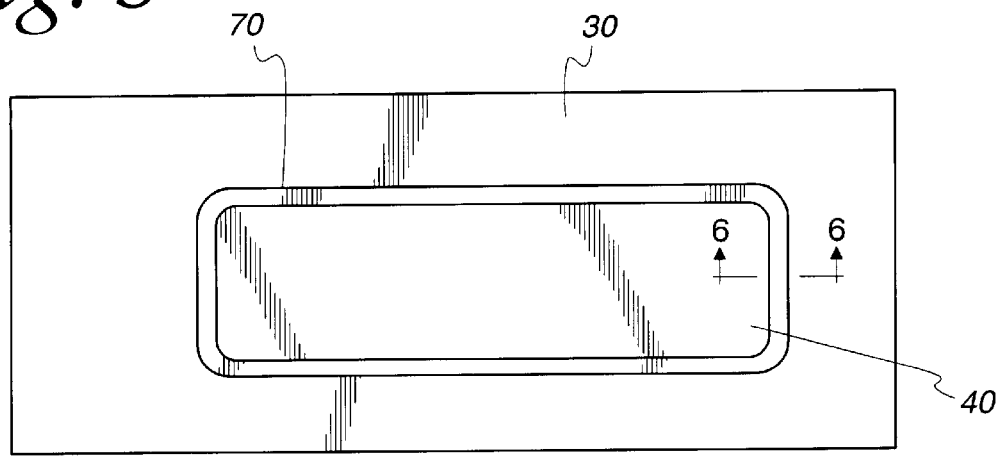
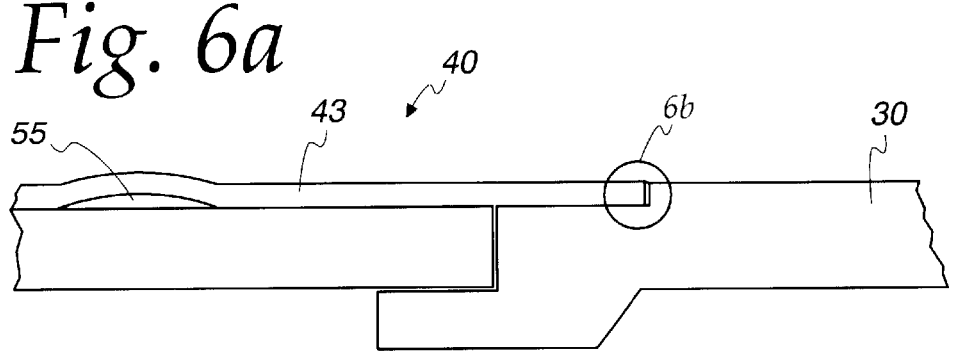
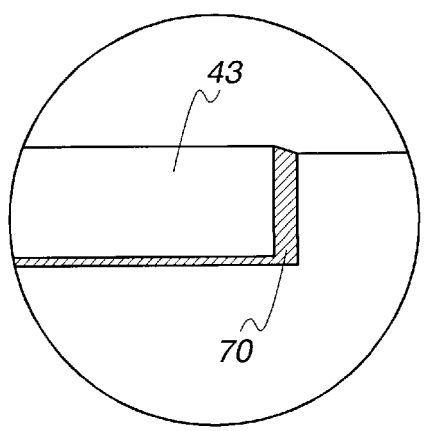

TRANSESOPHAGEAL PROBE WITH IMPROVED CONTROL PANEL

BACKGROUND OF THE INVENTION

This invention related to transesophageal probes, and more particularly relates to control panels for such probes.

Referring to FIG. 1, a conventional multiplane ultrasound transesophageal probe 20 typically includes an endoscope 24, a deflection section 26, an ultrasound transducer 28 and a control handle 30. A user typically manipulates various controls located on the handle in order to perform functions such as altering scan plane rotation of the transducer, biplane function, and three dimensional scan. In general, during a typical patient procedure, the transducer must be positioned from the controls on the handle while the transducer is located out of sight inside the patient. During the procedure, the transducer must be controlled to perform various functions.

The most common user interface for rotating the scan plane of transducer 28 (by motor) on a multiplane transesophageal probe requires the use of pushbutton switches mounted on, or integrated into, control handle 30 of probe 20. All switches must be sealed to avoid fluid penetration into handle 30, which contains sensitive electronic and mechanical components. Normally, there is one switch for clockwise and another switch for counterclockwise rotation.

Conventional scan plane-control user interfaces for multiplane transesophageal (TE) probes typically consist of handle-mounted pushbutton switches manipulated by the user during the TE procedure. The pushbuttons are individually sealed to avoid fluid penetration into the control handle. The conventional switch technology often allows very little design freedom with regards to quantity, size and configuration of the switches. Also, adding more than two pushbuttons is expensive, and involves a proportional amount of complications with regards to space requirements, geometry and fluid sealing.

The present invention these problems and provides a solution.

BRIEF SUMMARY OF THE INVENTION

The preferred embodiment is useful in a transesophageal probe comprising a transducer and a control handle for the transducer. The control handle comprises a control panel coupled to a plurality of switches. Foil covers the switches and a seal couples the control panel and said control handle so that the switches are protected.

By using the described structure, the ergonomics of the probe can be substantially improved. In addition, the freedom of design of the control handle is increased and the sealing of the switches is simplified.

BRIEF DESCRIPTION OF THE DRAWINGS

FIG. 1 is a schematic block diagram of a conventional multiplane transesophageal probe into which a preferred embodiment of the invention may be incorporated.

FIG. 2 is a top plan view of a preferred form of control panel made in accordance with the invention.

FIG. 3 is a top plan view of various shapes which may be used for the control panel shown in FIG. 2.

FIG. 4 is a fragmentary side elevational view illustrating one mode of coordinating the shape of the handle shown in FIG. 1 with the control panel shown in FIG. 2.

FIG. 5 is a fragmentary top plan view of the control panel shown in FIG. 2 with parts such as the switches removed to reveal the sealing of the control panel.

FIG. 6 is a fragmentary cross-sectional view taken along 6—6 in FIG. 5 illustrating the sealing of the foil and control panel shown in FIGS. 4–5.

DETAILED DESCRIPTION OF THE INVENTION

Referring to FIG. 2, a preferred form of handle 30 incorporates a control panel 40 including push button switches 51–58. Switch 51 controls the three dimensional scan of transducer 28 (FIG. 1). Switches 52–53 are user defined. Switches 54–57 control the scan plane of transducer 28, and switch 58 controls the biplane operation of transducer 28. By using the arrangements of control panel 40 shown in FIGS. 2–5, handle 30 may implement a more ergonomic user interface, as well as enabling the implementation of both factory- and user-defined controls. Control panel 40 can be utilized to replace conventional switches in order to simplify the fluid sealing of the scan plane controls. Locating all electronic user interface functions on a control panel 40 provides improvements in 1) Ergonomy, 2) Switch configuration design freedom and 3) Fluid sealing.

The control 40 includes printed circuit board (PCB) 42 configured with switches 51–58. The electrical connections with the PCB are made with a flat cable or a flexprint. Control panel 40 and switches 51–58 are covered with a water- and chemical resistant polymeric foil 43 with permanent markings shown in FIG. 2 to indicate the dedicated functions of each switch.

Referring to FIG. 3, the shape of control panel 40 can be optimized to provide the best possible ergonomy with the actual design of handle 30. For example, control panel may be configured as a modified rectangle 61 as shown in FIG. 2, an ellipse 62 or a modified L shape 63.

The pushbutton configuration (quantity, location and shape) of switches 51–58 can be adapted to meet the requirements of the specific application. By using the control panel design techniques shown in the drawings, control panel 40 can be designed to match the topography of handle 30. Referring to FIG. 2, handle 30 has a longitudinal axis LA and a transverse axis TA which are perpendicular to each other. Handle 30 could be curved along either the longitudinal or transversal axis, or alternatively, along both axes LA and TA. As shown in FIG. 4, handle 30 may have a curved top surface 32. The surface topography of surface 42 of control panel 40 is coordinated with the surface topography of top surface 32 as shown in FIG. 4. According to the example of FIG. 4, the radius of curvature of surface 32 is the same as the radius of curvature of surface 42. Surface 42 may be flush with surface 32 as shown in FIG. 4. Alternatively, surface 42 may extend above surface 32, or surface 42 may be below surface 32.

Whether control panel 40 is flat or curved, the switches can be configured any desired way within the physical limits of the panel, and there are few limitations with regards to button shape and size. Reconfiguration costs are low, as opposed to the conventional design where changes affect the handle design itself.

Referring to FIGS. 5 and 6, a fluid seal 70 coupling control panel 40 and handle 30 is achieved by gluing, or alternatively mechanically sealing, cover foil 43 and control panel 40 with handle 30. As a result of seal 70, the entire PCB with switches 51–58 resides in a dry area inside handle 30 by design, regardless of switch quantity or configuration.

Preferably, control panel 40 mounts all electronic user interface functions of the transesophageal (TE) probe 20, such as scan plane rotation, biplane function, three dimensional scan and other factory- or user-defined (programmable) controls. Key benefits are ergonomics, freedom of design (switch design/configuration) and simplified fluid sealing.

Those skilled in the art will recognize that the preferred embodiments may be modified and altered without departing from the true spirit and scope of the invention as defined in the accompanying claims.

What is claimed is:

1. A transesophageal probe comprising:
    a transducer; and
    a control handle for said transducer, said control handle having a predetermined surface topography and comprising
    a control panel;
    a plurality of switches coupled to said control panel and arranged to control movement of the transducer;
    foil covering said switches; and
    a seal coupling said control panel and said control handle, whereby said switches are protected.

2. A probe, as claimed in claim 1, wherein said control panel has a surface topography coordinated with the surface topography of said control handle.

3. A probe, as claimed in claim 1, wherein said control panel is curved along a first axis.

4. A probe, as claimed in claim 3, wherein said control panel is curved along a second axis perpendicular to said first axis.

5. A probe, as claimed in claim 1, wherein said control panel comprises a printed circuit board.

6. A probe, as claimed in claim 5, wherein said switches are mounted on said printed circuit board.

7. A probe, as claimed in claim 1, wherein said foil comprises a water and chemically resistant polymer.

8. A probe, as claimed in claim 1, wherein at least some of said plurality of switches comprise push button switches.

9. A probe, as claimed in claim 1, wherein said seal further couples said foil to said control handle.

10. A probe, as claimed in claim 1, wherein said seal comprises glue.

11. A probe, as claimed in claim 1 wherein said seal comprises a mechanical seal.

12. A probe, as claimed in claim 1, wherein said switches control at least in part positioning of said transducer.

13. A probe, as claimed in claim 1, wherein said switches control at least in part the functioning of said transducer.

14. A probe, as claimed in claim 1, wherein said transducer comprises an ultrasound transducer.

* * * * *